(12) United States Patent
Yang

(10) Patent No.: US 11,020,049 B2
(45) Date of Patent: Jun. 1, 2021

(54) METHOD AND DEVICE FOR DETECTING OSAHS

(71) Applicant: Song Yang, Guangzhou (CN)

(72) Inventor: Song Yang, Guangzhou (CN)

( * ) Notice: Subject to any disclaimer, the term of this patent is extended or adjusted under 35 U.S.C. 154(b) by 315 days.

(21) Appl. No.: 16/131,055

(22) Filed: Sep. 14, 2018

(65) Prior Publication Data

US 2019/0008452 A1 Jan. 10, 2019

Related U.S. Application Data

(63) Continuation of application No. PCT/CN2017/076664, filed on Mar. 14, 2017.

(30) Foreign Application Priority Data

Mar. 17, 2016 (CN) .......................... 201610158552.4

(51) Int. Cl.
*A61B 5/08* (2006.01)
*A61B 5/00* (2006.01)
(Continued)

(52) U.S. Cl.
CPC .......... *A61B 5/4818* (2013.01); *A61B 5/0816* (2013.01); *A61B 5/4812* (2013.01);
(Continued)

(58) Field of Classification Search
CPC ........... A61B 5/00; A61B 5/08; A61B 5/7242; A61B 5/0816; A61B 5/4818;
(Continued)

(56) References Cited

U.S. PATENT DOCUMENTS 8,365,729 B2\* 2/2013 Alder .................. A61B 5/4818
128/204.23
2005/0065560 A1 3/2005 Lee et al.
(Continued)

FOREIGN PATENT DOCUMENTS

CN 101365383 A 2/2009
CN 103190910 A 7/2013
(Continued)

OTHER PUBLICATIONS

Shuzhen Chen, the International Searching Authority written comments, May 2017, CN.

*Primary Examiner* — Eric J Messersmith

(57) ABSTRACT

A method and a device for detecting OSAHS provided that the method comprises: acquiring a vibration signal of a subject during sleep, and determining a breathing signal of the subject (S1), wherein the breathing signal comprises an inspiration signal generated upon inspiration and an expiration signal generated upon expiration; acquiring strength of a first vibration signal within a specified frequency range and superimposed on the inspiration signal, and strength of a second vibration signal within a specified frequency range and superimposed on the expiration signal adjacent to the inspiration signal (S2); and comparing, according to a preset method, the strength of the first vibration signal with the strength of the second vibration signal, and determining, according to a comparison result, whether the subject is snoring (S3). Since the detection is performed synchronously with breathing, the invention can prevent interference caused by coughing, speaking and other acoustic signals transmitted in the air, thereby significantly increasing accuracy in determining OSAHS. Moreover, the method and device of the invention can be realized by only making a minor modification to software in existing sleep sensors without incurring additional hardware costs.

6 Claims, 4 Drawing Sheets

(51) Int. Cl.
   *A61B 5/087*    (2006.01)
   *A61B 5/113*    (2006.01)
   *A61B 7/00*     (2006.01)

(52) U.S. Cl.
   CPC ............ *A61B 5/7242* (2013.01); *A61B 5/087* (2013.01); *A61B 5/113* (2013.01); *A61B 5/4815* (2013.01); *A61B 5/6892* (2013.01); *A61B 5/725* (2013.01); *A61B 7/003* (2013.01); *A61M 2205/3375* (2013.01)

(58) Field of Classification Search
   CPC ....... A61B 5/4812; A61B 5/087; A61B 7/003; A61B 5/6892; A61B 5/725; A61B 5/4815; A61B 5/113; A61M 2205/3375
   See application file for complete search history.

(56) References Cited

U.S. PATENT DOCUMENTS

2011/0190594 A1* 8/2011 Heit .................... A61B 5/4815
                                                        600/301
2016/0286974 A1* 10/2016 Boyd ................... A47C 27/083

FOREIGN PATENT DOCUMENTS

| CN | 103961105 A | 8/2014 |
| CN | 104739413 A | 7/2015 |
| CN | 105147244 A | 12/2015 |
| CN | 105615884 A | 6/2016 |

\* cited by examiner

METHOD AND DEVICE FOR DETECTING OSAHS

CROSS-REFERENCE TO RELATED APPLICATION

The present application is a continuation-application of International Application PCT/CN2017/076664, with an international filing date of Mar. 14, 2017, which claims foreign priority of Chinese Patent Application No. 201610158552.4, filed on Mar. 17, 2016 in the State Intellectual Property Office of China, the contents of all of which are hereby incorporated by reference.

BACKGROUND

1. Technical Field

The present disclosure generally relates to OSAHS detection fields, and especially relates to a method and a device for detecting OSAHS.

2. Description of Related Art

OSAHS (also called as snoring, sleep-apnea, obstructive sleep apnea-hypopnea syndrome, etc.) is a common sleep associated phenomenon. At present, most people think that it is common and seemed to think nothing of it, and even some people regard it as a sign of good sleep. However, snoring is harmful to health. Sleep-apnea due to snoring can cause severe hypoxia of brain and blood to result in hypoxemia, which may induce hypertension, brain heart disease, arrhythmia, myocardial infarction, angina, etc. If the duration of the sleep-apnea exceeds 120 seconds, it is prone sudden death in the early morning.

Therefore, it is necessary to effectively evaluate OSAHS to prevent a subject from snoring. A conventional vibrating device is set in a pillow or a mattress to detect OSAHS. When the subject is detected to be snoring, the vibration device can be activated to change sleep position of the subject or wake up the subject in order to effectively prevent the subject from snoring. However, in the related art, the detection of snoring condition is generally determined by detecting the sound from human's mouth. In this way, a miscalculation is triggered when the subject is speaking or external sound overlaps with judgment criteria. Thus, the conventional device for detecting OSAHS has the problem of a low specificity.

SUMMARY

The technical problems to be solved: in view of the shortcomings of the related art, the present disclosure relates to a method and a device for detecting OSAHS which can more accurately detect OSAHS than sound waves.

The technical solution adopted for solving technical problems of the present disclosure is:

a method for detecting OSAHS using a bedding. The method includes at least one microprocessor, a micro signal sensor and a memory of the bedding executing the steps below: acquiring a vibration signal of a subject during sleep, and determining a breathing signal of the subject, wherein the breathing signal includes an inspiration signal generated upon inspiration and an expiration signal generated upon expiration; acquiring strength of a first vibration signal within a specified frequency range and superimposed on the inspiration signal, and strength of a second vibration signal within a specified frequency range and superimposed on the expiration signal adjacent to the inspiration signal; comparing the strength of the first vibration signal with the strength of the second vibration signal according to a preset method, and determining whether the subject is snoring according to a comparison result; and wherein the specified frequency range and the preset method are respectively set and stored in the memory.

Wherein the step of comparing the strength of the first vibration signal with the strength of the second vibration signal according to a preset method, and determining whether the subject is snoring according to a comparison result includes: respectively processing strength integration of the first vibration signal and strength integration of the second vibration signal, and comparing the strength integration of the first vibration signal with the strength integration of the second vibration signal, and then determining whether the subject is snoring according to the comparison result.

Wherein the step of comparing the strength of the first vibration signal with the strength of the second vibration signal according to a preset method, and determining whether the subject is snoring according to a comparison result includes: calculating ratio of the strength of the first vibration signal and the strength of the second vibration signal; and comparing the obtained ratio with a preset threshold stored in the memory, and determining whether the subject is snoring according to a comparison result.

Wherein the step of comparing the obtained ratio with a preset threshold stored in the memory, and determining whether the subject is snoring according to a comparison result includes: determining the subject is snoring when the ratio by dividing the strength of the first vibration signal by the strength of the second vibration signal is greater than or equal to a first preset threshold stored in the memory; and determining the subject is snoring when the ratio by dividing the strength of the second vibration signal by the strength of the first vibration signal is less than or equal to a second preset threshold stored in the memory.

Wherein the step of comparing the obtained ratio with a preset threshold stored in the memory, and determining whether the subject is snoring according to a comparison result includes: calculating ratio of the strength of the first vibration signal and the strength of the second vibration signal and comparing the obtained ratio with the preset threshold stored in the memory; and determining the subject is snoring when the continuous specified number of times of the comparison result is consistent with the characteristics of snoring status.

A device for detecting OSAHS using a bedding according to an exemplary embodiment of the present disclosure, the bedding includes at least one microprocessor, a micro signal sensor and a memory, with a specified frequency range and a preset method respectively set and stored in the memory. The at least one microprocessor includes a first acquiring unit configured to acquire a vibration signal of a subject during sleep, and determining a breathing signal of the subject, wherein the breathing signal comprises an inspiration signal generated upon inspiration and an expiration signal generated upon expiration; a second acquiring unit configured to acquiring strength of a first vibration signal within a specified frequency range and superimposed on the inspiration signal, and strength of a second vibration signal within a specified frequency range and superimposed on the expiration signal adjacent to the inspiration signal; and a determining unit configured to compare the strength of the first vibration signal with the strength of the second vibration signal according to the preset method, and determine whether the subject is snoring according to a comparison result.

Wherein the determining unit includes an integral module configured to respectively process strength integration of the first vibration signal and strength integration of the second vibration signal, and compare the strength integration of the first vibration signal with the strength integration of the second vibration signal, and then determine whether the subject is snoring according to the comparison result.

Wherein the determining unit further includes a ratio processing module configured to calculate ratio of the strength of the first vibration signal and the strength of the second vibration signal; and a determining module configured to compare the obtained ratio with a preset threshold stored in the memory and then determine whether the subject is snoring according to a comparison result.

Wherein the determining module includes a first determining submodule configured to determine the subject is snoring when the ratio by dividing the strength of the first vibration signal by the strength of the second vibration signal is greater than or equal to a first preset threshold stored in the memory; or a second determining submodule configured to determine the subject is snoring when the ratio by dividing the strength of the second vibration signal by the strength of the first vibration signal is less than or equal to a second preset threshold stored in the memory.

Wherein the determining module further includes a third determining submodule configured to calculate ratio of the strength of the first vibration signal and the strength of the second vibration signal and compare the obtained ratio with the preset threshold stored in the memory; and then determine the subject is snoring when the continuous specified number of times of the comparison result is consistent with the characteristics of snoring status.

The present disclosure provides the advantages as below.

The structure of the present disclosure can determine whether the subject is snoring by comparing the strength of a first vibration signal within a specified frequency range and superimposed on the inspiration signal and the strength of a second vibration signal within a specified frequency range and superimposed on the expiration signal adjacent to the inspiration signal. Since the inspiration signal is collected is contact sensors so that the detection is synchronously performed with breathing, which can prevent interference caused by coughing, speaking and other acoustic signals transmitted in air, thereby significantly increasing accuracy in determining OSAHS. At the same time, the method and the device of the prevent disclosure can be realized by only making a minor modification to software in existing sleep sensors (micro signal sensors set in a bedding) without incurring additional hardware costs. Moreover, the added software module is also very simple to only perform the detection and filtering of high-frequency signals with different phases of inspiration signals, and then perform the division operation.

BRIEF DESCRIPTION OF THE DRAWINGS

Many aspects of the embodiments can be better understood with reference to the following drawings. The components in the drawings are not necessarily dawns to scale, the emphasis instead being placed upon clearly illustrating the principles of the embodiments. Moreover, in the drawings, like reference numerals designate corresponding parts throughout the several views.

Figure 1:
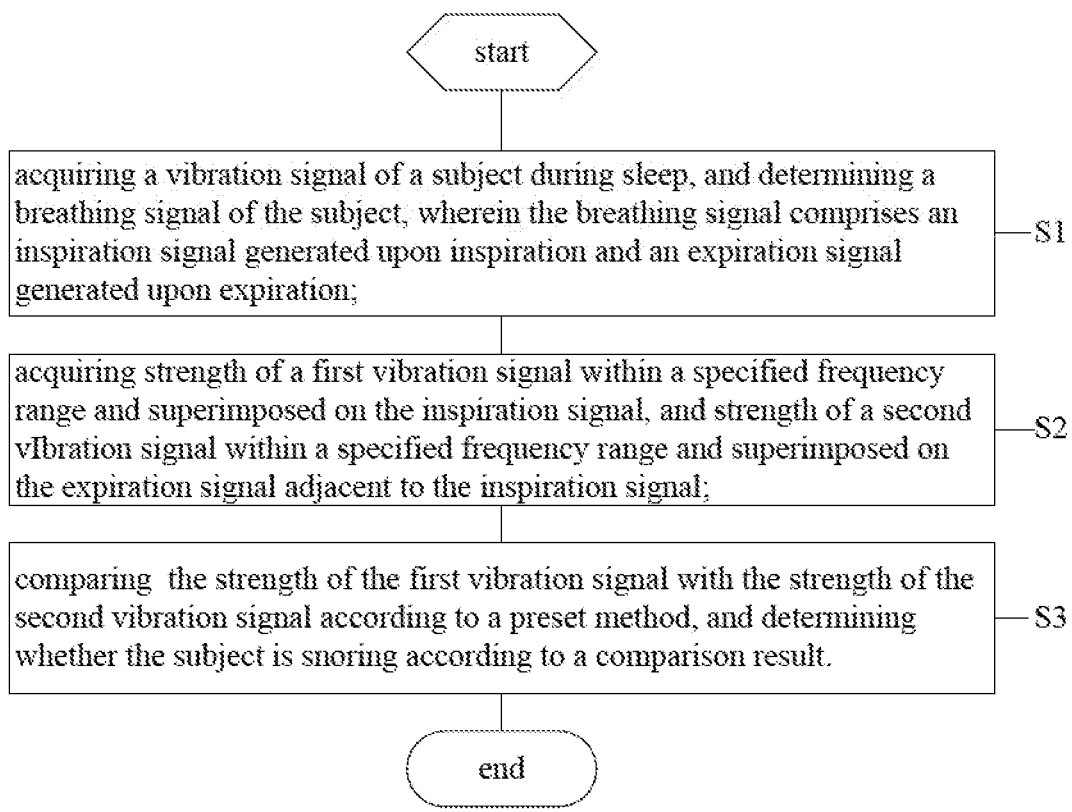
FIG. 1 is a flow chart of the method for detecting OSAHS in accordance with an exemplary embodiment.

The technical problems, features and advantages of the present disclosure are described in further detail with reference to the accompanying drawings.

DETAILED DESCRIPTION

The disclosure is illustrated by way of example and not by way of limitation in the figures of the accompanying drawings, in which like reference numerals indicate similar elements.

Figure 2:
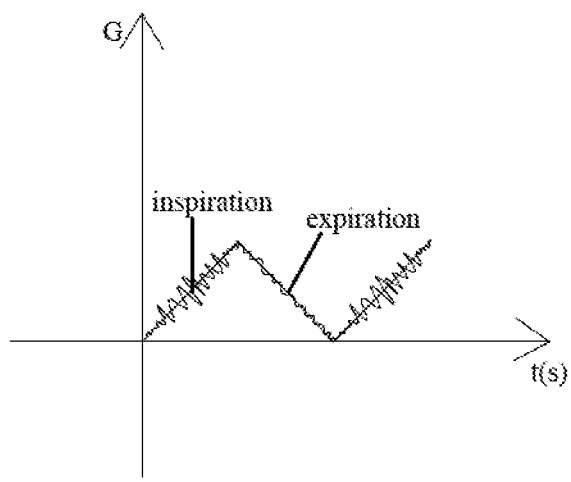
FIG. 2 is a schematic view of signals status of breathing signals of FIG. 1, shown in OSAHS.
Figure 3:
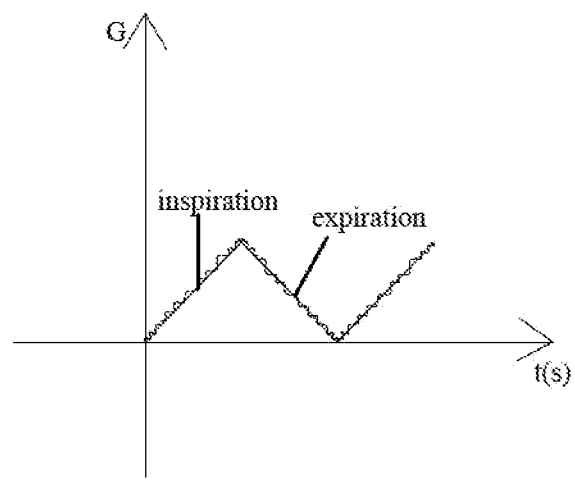
FIG. 3 is a schematic view of signals status of breathing signals of FIG. 1, shown the subject is snoring.

Referring to FIGS. 1-3, a method for detecting OSAHS in accordance with an exemplary embodiment includes the following steps below:

Step S1, acquiring a vibration signal of a subject during sleep, and determining a breathing signal of the subject, wherein the breathing signal includes an inspiration signal generated upon inspiration, with a corresponding electrical signal to the inspiration signal being shown as a baseline ascent curve of 1-3 seconds, and an expiration signal generated upon expiration, with a corresponding electrical signal to the expiration signal being shown as a baseline descent curve of 1-3 seconds;

Step S2, acquiring strength of a first vibration signal within a specified frequency range and superimposed on the inspiration signal, with the corresponding electrical signal to the inspiration signal being represented a higher frequency signal near 300 Hz and superimposed on the baseline of the inspiration signal, and strength of a second vibration signal within a specified frequency range and superimposed on the expiration signal adjacent to the inspiration signal, with the corresponding electrical signal to the expiration signal being represented a higher frequency signal near 300 Hz and superimposed on the baseline of the expiration signal;

Step S3, comparing the strength of the first vibration signal with the strength of the second vibration signal according to a preset method, and then determining whether the subject is snoring according to a comparison result.

Figure 7:
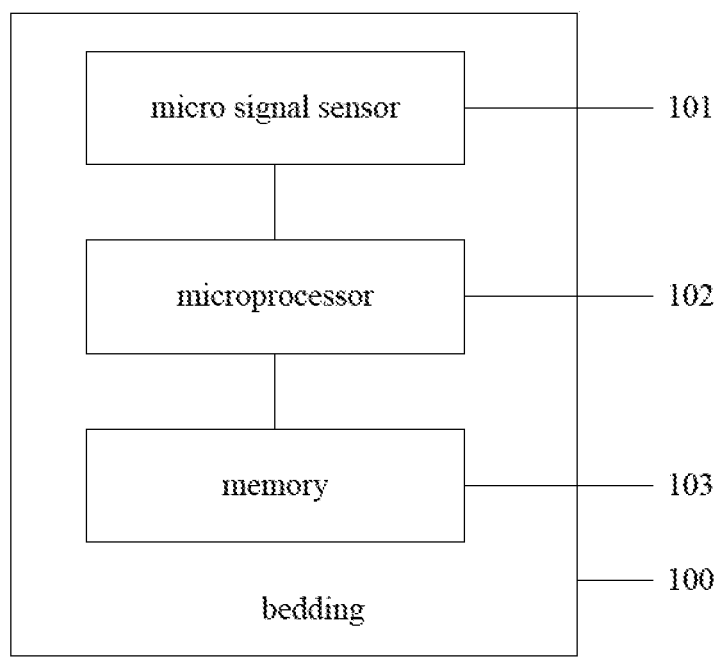
FIG. 7 is a schematic view of the device for detecting OSAHS using a bedding of FIG. 1.

As described in the step S1 above, the method for acquiring the vibration signal of the subject during sleep can be performed by a micro signal sensor set in a bedding 100 (shown in FIG. 7). The vibration signal generally includes information of heartbeat, breathing and turning over. The method of the present disclosure can acquire the breathing signals only by means of detection, filtering and the like. The breathing signal above includes the inspiration signal and the expiration signal. That is, it includes a process within a breathing cycle of the subject. For example, from inspiration to expiration, or from expiration to inspiration, is the breathing cycle of the subject. When the subject is snoring, the breathing of the subject is mainly impeded so that a "snoring" sound is produced. However, the "snoring" sound can't be occurred during expiration, so it can facilitate subsequent analysis via carefully distinguishing the breathing signals.

In an exemplary embodiment of the present disclosure, the bedding 100 is a pillow or a mattress.

As described in the step S2 above, during sleep, a breathing frequency of the subject is generally from 0.2 Hz to 0.5 Hz. When the subject is snoring, a vibration signal within 200 Hz~300 Hz is appeared and superimposed on the breathing signal. That is to more accurately say, the vibration signal is superimposed on the inspiration signal. In this way, the strength of the vibration signal within 200 Hz~300 Hz superimposed on the inspiration signal can reflect whether the subject is snoring during sleep.

As described in the step S3 above, referring to FIG. 2, when the subject is snoring, the strength of the first vibration signal superimposed on the inspiration signal is significantly different from the strength of the second vibration signal superimposed on the expiration signal. For example, the strength of the first vibration signal is significantly greater than the strength of the second vibration signal. Referring to FIG. 3, when the strength of the first vibration signal is substantially same as the strength of the second vibration signal, it can be indicated that the subject is not snoring. The preset method above mentioned includes a variety of ways, for example, the strength of the first vibration signal is subtracted from the strength of the second vibration signal to obtain a result, and then an absolute value of the result is compared with a preset threshold, and the subject can be considered to be snoring if the absolute value of the result is greater than or equal to the preset threshold.

In an exemplary embodiment of the present disclosure, the step S3 of comparing the strength of the first vibration signal with the strength of the second vibration signal according to the preset method, and determining whether the subject is snoring according to a comparison result includes:

Step S31, respectively processing strength integration of the first vibration signal and strength integration of the second vibration signal, and comparing the strength integration of the first vibration signal with the strength integration of the second vibration signal, and then determining whether the subject is snoring according to the comparison result.

As described in the step S31 above, the respective strength integration of the first vibration signal and the second vibration signal can obtain two results respectively equivalent to the two strengths. In this way, it can more intuitively obtain the results and convenient to compare the two data.

Figure 4:
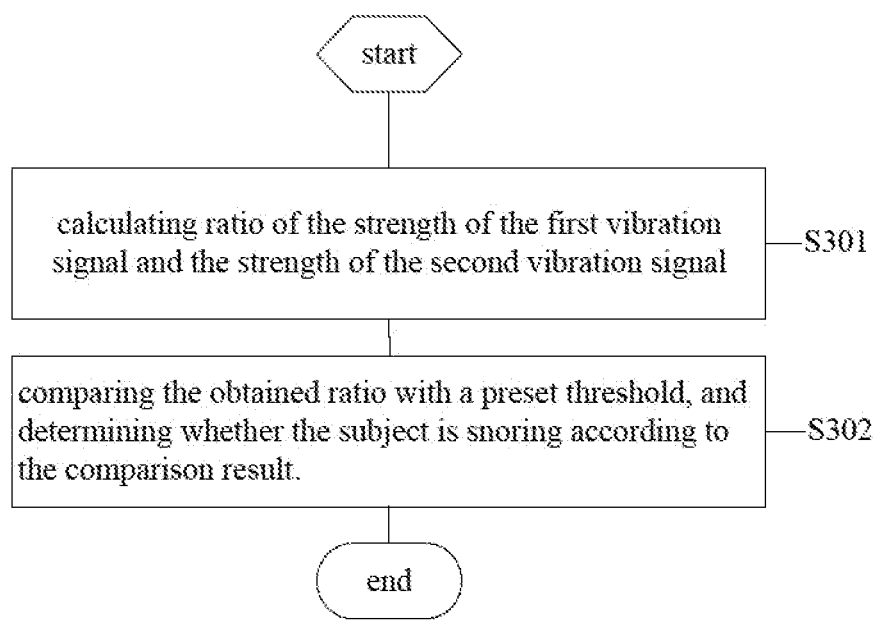
FIG. 4 is flow chart of the method for determining whether the subject is snoring according to a comparison result of FIG. 1.

Referring to FIG. 4, in an exemplary embodiment of the present disclosure, the step S3 of comparing the strength of the first vibration signal with the strength of the second vibration signal according to the preset method, and determining whether the subject is snoring according to a comparison result further includes:

Step S301, calculating ratio of the strength of the first vibration signal and the strength of the second vibration signal;

Step S302, comparing the obtained ratio with the preset threshold, and determining whether the subject is snoring according to the comparison result.

As described in the step S301 above, during normal sleep, the strength of the first vibration signal is substantially same as the strength of the second vibration signal so that the ratio between the two strengths is about 1.

As described in the step S302 above, when the subject is snoring, the ratio between the two strengths is greater than one specified threshold or less than another specified threshold. In this way, the result of the ratio depends on which one of the strength of the first vibration signal and the strength of the second vibration signal is as a denominator. For example, in an exemplary embodiment of the present disclosure, the subject is determined to be snoring when the ratio by dividing the strength of the first vibration signal by the strength of the second vibration signal is greater than or equal to a first preset threshold. In an exemplary embodiment of the present disclosure, the first preset threshold is typically 1.5. In another exemplary embodiment of the present disclosure, the subject is determined to be snoring when the ratio by dividing the strength of the second vibration signal by the strength of the first vibration signal is less than or equal to a second preset threshold. In an exemplary embodiment of the present disclosure, the second preset threshold is typically 0.67.

In an exemplary embodiment of the present disclosure, the step S302 of comparing the strength of the first vibration signal with the strength of the second vibration signal according to a preset method, and determining whether the subject is snoring according to a comparison result includes:

Step S3021, calculating ratio of the strength of the first vibration signal and the strength of the second vibration signal and comparing the obtained ratio with the preset threshold; and determining the subject is snoring when the continuous specified number of times of the comparison result is consistent with the characteristics of snoring status.

As described in the step S3021 above, the above continuous specified number of times of the comparison result is consistent with the characteristics of snoring status, which is referred that, during in several successive breathing cycles, the ratio between the strengths of the first and second vibration signals of each breathing signal is calculated and then compared with the preset threshold, and the comparison result is indicated that the subject may be in a snoring status during sleep, so the subject is determined to be snoring. Since the detection is synchronously performed with breathing movements, and the subject is determined to be snoring when a plurality of breathing movements is consistent with the characteristics of snoring status, it can prevent interference caused by coughing and speaking etc. At the same time, since other vibration signals are difficultly synchronized with the breathing movements for many times, it is difficult to cause false identification and greatly improve the identification accuracy of the snoring status.

In an exemplary embodiment of the present disclosure, referring to FIG. 7, a vibration device and a device for detecting OSAHS are respectively installed in a bedding 100. The vibration device is controlled to vibrate when the subject is detected to be snoring by the device for detecting OSAHS. The bedding 100 with the device for detecting OSAHS includes some hardware structures such as a micro signal sensor 101, at least one microprocessor 102 and a memory 103. The micro signal sensor 101 and the memory 103 are respectively and electrically connected to the at least one microprocessor 102. The specified frequency range, the preset method and the preset threshold are respectively set and stored in the memory 103. In this condition, when the head of the subject presses onto the bedding 100, the micro signal sensor 101 can collect vibration signals of the subject. Its detection process includes the following below:

First, collecting a micro signal of a subject and acquiring a breathing signal of the micro signal by the micro signal sensor;

Second, acquiring a first vibration signal with a frequency of 150 Hz and superimposed on the inspiration signal of the breathing signal, and acquiring a second vibration signal with a frequency of 150 Hz and superimposed on the expiration signal of the breathing signal by the device for detecting OSAHS;

Third, respectively processing the strength integration of the first vibration signal and the second vibration signal, and respectively obtaining a first result represented the strength of the first vibration signal and a second result represented the strength of the second vibration signal;

Fourth, dividing the first result by the second result to obtain a ratio, and determining the subject is consistent with the characteristics of snoring status if the ratio is greater than or equal to 1.5;

Fifth, if each ratio in five successive breathing cycles is greater than or equal to 1.5, determining the subject is snoring, and then controlling the vibration device to vibrate and changing a position of the head of the subject to prevent the subject from being snoring.

The method for detecting OSAHS of the present disclosure, since the detection is synchronously performed with breathing movements, and the subject is determined to be snoring when a plurality of breathing movements is consistent with the characteristics of snoring status, it can prevent interference caused by coughing and speaking etc. At the same time, since other vibration signals are difficultly synchronized with the breathing movements for many times, it is difficult to cause false identification and greatly improve the identification accuracy of the snoring status. Furthermore, the method of the prevent disclosure can be realized by only making a minor modification to software in existing sleep sensors (micro signal sensors set in the bedding 100) without incurring additional hardware costs. Moreover, the added software module is also very simple to only perform the detection and filtering of high-frequency signals with different phases of inspiration signals, and then perform the division operation.

Figure 5:
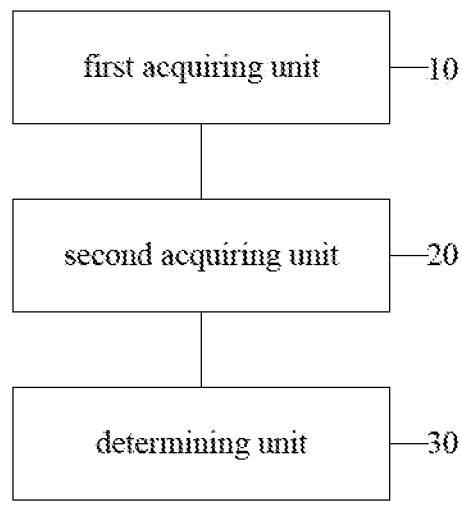
FIG. 5 is a schematic view of the device for detecting OSAHS in accordance with an exemplary embodiment.
Figure 6:
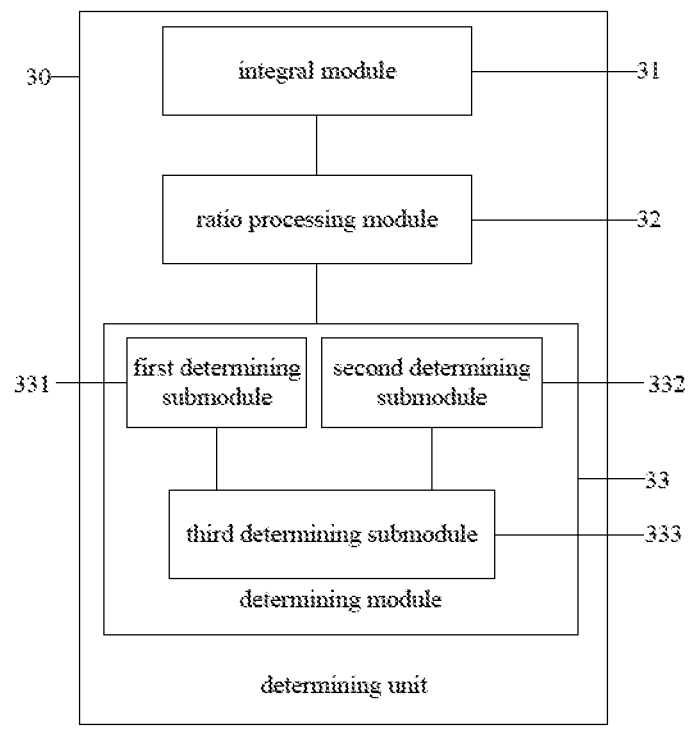
FIG. 6 is a schematic view of a determining unit of the device for detecting OSAHS of FIG. 1.

Referring to FIGS. 5-7, a device for detecting OSAHS used in a bedding 100 according to an exemplary embodiment of the present disclosure is provided. The bedding 100 includes a micro signal sensor 101, at least one microprocessor 102 and a memory 103. The micro signal sensor 101 and the memory 103 are respectively and electrically connected to the at least one microprocessor 102. The specified frequency range, the preset method and the preset threshold are respectively set and stored in the memory 103. The at least one microprocessor 102 includes:

A first acquiring unit 10 is configured to acquire a vibration signal of a subject during sleep, and determine a breathing signal of the subject, wherein the breathing signal includes an inspiration signal (generated upon inspiration, with a corresponding electrical signal to the inspiration signal being shown as a baseline ascent curve of 1-3 seconds, and an expiration signal generated upon expiration, with a corresponding electrical signal to the expiration signal being shown as a baseline descent curve of 1-3 seconds;

A second acquiring unit 20 is configured to acquire strength of a first vibration signal within a specified frequency range and superimposed on the inspiration signal, with the corresponding electrical signal to the inspiration signal being represented a higher frequency signal near 300 Hz and superimposed on the baseline of the inspiration signal, and strength of a second vibration signal within a specified frequency range and superimposed on the expiration signal adjacent to the inspiration signal, with the corresponding electrical signal to the expiration signal being represented a higher frequency signal near 300 Hz superimposed on the baseline of the expiration signal;

A determining unit 30 is configured to compare the strength of the first vibration signal with the strength of the second vibration signal according to a preset method, and then determine whether the subject is snoring according to a comparison result.

As the first acquiring unit 10 shown above, the method for acquiring the vibration signal of the subject during sleep can be performed by the micro signal sensor 101 set in the bedding 100. The vibration signal generally includes information of heartbeat, breathing and turning over. The method of the present disclosure can acquire the breathing signals only by means of detection, filtering and the like. The breathing signal above includes the inspiration signal and the expiration signal. That is, it includes a process within a breathing cycle of the subject. For example, from inspiration to expiration, or from expiration to inspiration, is the breathing cycle of the subject. When the subject is snoring, the breathing of the subject is mainly impeded so that a "snoring" sound is produced. Otherwise, the "snoring" sound can't be occurred during expiration, so it can facilitate subsequent analysis via carefully distinguishing the breathing signals.

As the second acquiring unit 20 shown above, during sleep, a breathing frequency of the subject is generally from 0.2 Hz to 0.5 Hz. When the subject is snoring, a vibration signal within 200 Hz~300 Hz is appeared and superimposed on the breathing signal. That is to more accurately say, the vibration signal is superimposed on the inspiration signal. In this way, the strength of the vibration signal within 200 Hz~300 Hz and superimposed on the inspiration signal can reflect whether the subject is snoring during sleep. The strength of the first vibration signal superimposed on the inspiration signal is significantly different from the strength of the second vibration signal superimposed on the expiration signal, when the subject is snoring. While, when the strength of the first vibration signal is substantially same as the strength of the second vibration signal, the subject is not snoring.

As the determining unit 30 shown above, referring to FIG. 2, when the subject is snoring, the strength of the first vibration signal superimposed on the inspiration signal is significantly different from the strength of the second vibration signal superimposed on the expiration signal. For example, the strength of the first vibration signal is significantly greater than the strength of the second vibration signal. Referring to FIG. 3, when the strength of the first vibration signal is substantially same as the strength of the second vibration signal, the subject is not snoring. The preset method above mentioned includes a variety of ways, for example, the strength of the first vibration signal is subtracted from the strength of the second vibration signal to obtain a result, and then an absolute value of the result is compared with a preset threshold, and the subject can be considered to be snoring if the absolute value of the result is greater than or equal to the preset threshold.

Referring to FIG. 6, in an exemplary embodiment of the present disclosure, the determining unit 30 includes:

An integral module 31 is configured to respectively process strength integration of the first vibration signal and strength integration of the second vibration signal, and compare the strength integration of the first vibration signal with the strength integration of the second vibration signal, and then determine whether the subject is snoring according to the comparison result.

As the integral module 31 shown above, the respective strength integration of the first vibration signal and the second vibration signal can obtain two results respectively equivalent to the two strengths. In this way, it can more intuitively obtain the results and convenient to compare the two data.

In an exemplary embodiment of the present disclosure, the determining unit 30 further includes:

A ratio processing module 32 is configured to calculate ratio of the strength of the first vibration signal and the strength of the second vibration signal;

A determining module 33 is configured to compare the obtained ratio with the preset threshold, and determine whether the subject is snoring according to the comparison result.

As the ratio processing module 32 shown above, during normal sleep, the strength of the first vibration signal is substantially same as the strength of the second vibration signal so that the ratio between the two strengths is about 1.

As the determining module 33 shown above, when the subject is snoring, the ratio of the two strengths is greater than one specified threshold or less than another specified threshold. In this way, the result of the ratio depends on which one of the strength of the first vibration signal and the strength of the second vibration signal is as a denominator.

In an exemplary embodiment of the present disclosure, the determining module 33 includes a first determining submodule 331 configured to determine the subject is snoring when the ratio by dividing the strength of the first vibration signal by the strength of the second vibration signal is greater than or equal to a first preset threshold stored in the memory 103. In an exemplary embodiment of the present disclosure, the first preset threshold is typically 1.5. In another exemplary embodiment of the present disclosure, the determining module 33 includes a second determining submodule 332 configured to determine the subject is snoring when the ratio by dividing the strength of the second vibration signal by the strength of the first vibration signal is less than or equal to a second preset threshold stored in the memory 103. In an exemplary embodiment of the present disclosure, the second preset threshold is typically 0.67.

In an exemplary embodiment of the present disclosure, the determining module 33 shows above further includes:

A third determining submodule 333 is configured to calculate ratio of the strength of the first vibration signal and the strength of the second vibration signal and compare the obtained ratio with the preset threshold; and then determine the subject is snoring when the continuous specified number of times of the comparison result is consistent with the characteristics of snoring status.

As the third determining submodule 333 shown above, the above continuous specified number of times of the comparison result is consistent with the characteristics of snoring status, which is referred that, during in several successive breathing cycles, the ratio between the strengths of the first and second vibration signals of each breathing signal is calculated and then compared with the preset threshold stored in the memory 103, and the comparison result is indicated that the subject may be in a snoring status during sleep, so the subject is determined to be snoring. Since the detection is synchronously performed with breathing movements, and the subject is determined to be snoring when a plurality of breathing movements is consistent with the characteristics of snoring status, it can prevent interference caused by coughing and speaking etc. At the same time, since other vibration signals are difficultly synchronized with the breathing movements for many times, it is difficult to cause false identification and greatly improve the identification accuracy of the snoring status.

In an exemplary embodiment of the present disclosure, a vibration device and a device for detecting OSAHS are respectively installed in the bedding 100. The vibration device is controlled to vibrate when the subject is detected to be snoring by the device for detecting OSAHS. The bedding 100 with the device for detecting OSAHS includes some hardware structures such as a micro signal sensor 101, at least one microprocessor 102 and a memory 103. The micro signal sensor 101 and the memory 103 are respectively and electrically connected to the at least one microprocessor 102. The specified frequency range, the preset method and the preset threshold are respectively set and stored in the memory 103. In this condition, when the head of the subject presses onto the bedding 100, the micro signal sensor 101 can collect vibration signals of the subject. Its detection process includes the following below:

First, collecting a micro signal of a subject and acquiring a breathing signal of the micro signal by the micro signal sensor;

Second, acquiring a first vibration signal with a frequency of 150 Hz and superimposed on the inspiration signal of the breathing signal, and acquiring a second vibration signal with a frequency of 150 Hz and superimposed on the expiration signal of the breathing signal by the device for detecting OSAHS;

Third, respectively processing the strength integration of the first vibration signal and the second vibration signal, and respectively obtaining a first result represented the strength of the first vibration signal and a second result represented the strength of the second vibration signal;

Fourth, dividing the first result by the second result to obtain a ratio, and determining the subject is consistent with the characteristics of snoring status if the ratio is greater than or equal to 1.5;

Fifth, if each ratio in five successive breathing cycles is greater than or equal to 1.5, determining the subject is snoring, and then controlling the vibration device to vibrate and changing a position of the head of the subject to prevent the subject from being snoring.

The device for detecting OSAHS of the present disclosure, since the detection is synchronously performed with breathing movements, and the subject is determined to be snoring when a plurality of breathing movements is consistent with the characteristics of snoring status, it can prevent interference caused by coughing and speaking etc. At the same time, since other vibration signals are difficultly synchronized with the breathing movements for many times, it is difficult to cause false identification and greatly improve the identification accuracy of the snoring status. Furthermore, the device of the prevent disclosure can be realized by only making a minor modification to software in existing sleep sensors (micro signal sensors set in the bedding) without incurring additional hardware costs. Moreover, the added software module is also very simple to only perform the detection and filtering of high-frequency signals with different phases of inspiration signals, and then perform the division operation.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A method for detecting OSAHS using a bedding, the method comprising at least one microprocessor, a micro signal sensor and a memory of the bedding executing the steps of:

acquiring a vibration signal of a subject during sleep, and determining a breathing signal of the subject, wherein the breathing signal comprises an inspiration signal generated upon inspiration and an expiration signal generated upon expiration;

acquiring strength of a first vibration signal within a specified frequency range and superimposed on the inspiration signal, and strength of a second vibration signal within a specified frequency range and superimposed on the expiration signal adjacent to the inspiration signal;

comparing the strength of the first vibration signal with the strength of the second vibration signal according to a preset method, and determining whether the subject is snoring according to a comparison result; and wherein the specified frequency range and the preset method are respectively set and stored in the memory; and wherein the step of comparing the strength of the first vibration signal with the strength of the second vibration signal according to a preset method, and determining whether the subject is snoring according to a comparison result comprises: respectively processing strength integration of the first vibration signal and strength integration of the second vibration signal, and comparing the strength integration of the first vibration signal with the strength integration of the second vibration signal, and then determining whether the subject is snoring according to the comparison result; or calculating ratio of the strength of the first vibration signal and the strength of the second vibration signal; and comparing the obtained ratio with a preset threshold stored in the memory, and determining whether the subject is snoring according to a comparison result; and wherein the specified frequency range is 200 Hz-300 Hz, and the preset threshold is equal to 1.5 or 0.67.

2. The method for detecting OSAHS as claimed in claim 1, wherein the step of comparing the obtained ratio with a preset threshold stored in the memory, and determining whether the subject is snoring according to a comparison result comprises: determining the subject is snoring when the ratio by dividing the strength of the first vibration signal by the strength of the second vibration signal is greater than or equal to a first preset threshold stored in the memory; and determining the subject is snoring when the ratio by dividing the strength of the second vibration signal by the strength of the first vibration signal is less than or equal to a second preset threshold stored in the memory; and wherein the first preset threshold is equal to 1.5 and the second preset threshold is equal to 0.67.

3. The method for detecting OSAHS as claimed in claim 1, wherein the step of comparing the obtained ratio with a preset threshold stored in the memory, and determining whether the subject is snoring according to a comparison result comprises: calculating the ratio of the strength of the first vibration signal and the strength of the second vibration signal and comparing the obtained ratio with the preset threshold stored in the memory; and determining the subject is snoring when the continuous specified number of times of the comparison result is consistent with the characteristics of snoring status.

4. A device for detecting OSAHS using a bedding, the bedding comprising at least one microprocessor, a micro signal sensor and a memory, with a specified frequency range and a preset method respectively set and stored in the memory, the at least one microprocessor comprising:

a first acquiring unit configured to acquire a vibration signal of a subject during sleep, and determining a breathing signal of the subject, wherein the breathing signal comprises an inspiration signal generated upon inspiration and an expiration signal generated upon expiration;

a second acquiring unit configured to acquiring strength of a first vibration signal within a specified frequency range and superimposed on the inspiration signal, and strength of a second vibration signal within a specified frequency range and superimposed on the expiration signal adjacent to the inspiration signal; and a determining unit configured to compare the strength of the first vibration signal with the strength of the second vibration signal according to the preset method, and determine whether the subject is snoring according to a comparison result;

an integral module configured to respectively process strength integration of the first vibration signal and strength integration of the second vibration signal, and compare the strength integration of the first vibration signal with the strength integration of the second vibration signal, and then determine whether the subject is snoring according to the comparison result; or a ratio processing module configured to calculate ratio of the strength of the first vibration signal and the strength of the second vibration signal; and a determining module configured to compare the obtained ratio with a preset threshold stored in the memory and then determine whether the subject is snoring according to a comparison result; and wherein the specified frequency range is 200 Hz-300 Hz, and the preset threshold is equal to 1.5 or 0.67.

5. The device for detecting OSAHS as claimed in claim 4, wherein the determining module comprises a first determining submodule configured to determine the subject is snoring when the ratio by dividing the strength of the first vibration signal by the strength of the second vibration signal is greater than or equal to a first preset threshold stored in the memory; or a second determining submodule configured to determine the subject is snoring when the ratio by dividing the strength of the second vibration signal by the strength of the first vibration signal is less than or equal to a second preset threshold stored in the memory; and wherein the first preset threshold is equal to 1.5 and the second preset threshold is equal to 0.67.

6. The device for detecting OSAHS as claimed in claim 4, wherein the determining module further comprises a third determining submodule configured to calculate the ratio of the strength of the first vibration signal and the strength of the second vibration signal and compare the obtained ratio with the preset threshold stored in the memory; and then determine the subject is snoring when the continuous specified number of times of the comparison result is consistent with the characteristics of snoring status.

* * * * *